United States Patent
Xing et al.

(10) Patent No.: US 10,252,985 B2
(45) Date of Patent: Apr. 9, 2019

(54) SOLVENT-FREE GREEN AMMOXIMATION PROCESS BASED ON FILM DISTRIBUTION

(71) Applicant: Nanjing University of Technology, Nanjing, Jiangsu Province (CN)

(72) Inventors: Weihong Xing, Nanjing (CN); Honglin Mao, Nanjing (CN); Rizhi Chen, Nanjing (CN); Hongnian Shang, Nanjing (CN); Nanping Xu, Nanjing (CN)

(73) Assignee: Nanjing University of Technology (CN)

( * ) Notice: Subject to any disclaimer, the term of this patent is extended or adjusted under 35 U.S.C. 154(b) by 0 days.

(21) Appl. No.: 16/062,630

(22) PCT Filed: Jul. 31, 2015

(86) PCT No.: PCT/CN2015/085752
§ 371 (c)(1),
(2) Date: Jun. 15, 2018

(87) PCT Pub. No.: WO2016/179910
PCT Pub. Date: Nov. 17, 2016

(65) Prior Publication Data
US 2019/0040003 A1   Feb. 7, 2019

(30) Foreign Application Priority Data

May 13, 2015   (CN) .......................... 2015 1 0242197

(51) Int. Cl.
*C07C 249/04* (2006.01)
*C07C 251/44* (2006.01)
*B01J 29/89* (2006.01)
*C07C 251/38* (2006.01)

(52) U.S. Cl.
CPC ............. *C07C 249/04* (2013.01); *B01J 29/89* (2013.01); *C07C 251/38* (2013.01); *C07C 251/44* (2013.01)

(58) Field of Classification Search
CPC ... C07C 249/00; C07C 249/04; C07C 249/08; B01J 29/89; B01J 35/023
See application file for complete search history.

(56) References Cited

U.S. PATENT DOCUMENTS

2014/0093437 A1* 4/2014 Del Seppia .............. B01J 8/006
                                                          422/187

* cited by examiner

*Primary Examiner* — Jafar F Parsa
(74) *Attorney, Agent, or Firm* — PROI Intellectual Property US

(57) ABSTRACT

The invention relates to a solvent-free green ammoximation process based on membrane distribution with a procedure as: adding TS-1 catalyst and ketone into a reactor in advance; setting the stirring speed and reaction temperature; after reaching the set temperature, adding a certain amount of ammonia and hydrogen peroxide into a reaction solution, wherein the hydrogen peroxide is fed in a way of using membrane as a distributor, the ammonia is fed in a continuous or semi-continuous manner; oxime is produced upon the reaction. The advantages of the invention include the mild reaction conditions, high reacting efficiency, simple operation and environmentally-friendly process. And there is no need to add any solvent during the reaction process. During the ammoximation reaction, both the conversion rate of the ketone and the selectivity of the oxime can be over 98.0%.

8 Claims, 1 Drawing Sheet

US 10,252,985 B2

SOLVENT-FREE GREEN AMMOXIMATION PROCESS BASED ON FILM DISTRIBUTION

TECHNICAL FIELD

The invention belongs to the field of chemical engineering process, and relates to a process for oxime production, in particular to a solvent-free green ammoximation process based on membrane distribution.

BACKGROUND

Oxime, such as cyclohexanone-oxime, diacetylmonoxime and acetoxime, is an important chemical intermediate that is used as an important raw material for synthesis of organosilicon crosslinking agent, as boiler deoxidizer and as antiskinning agent for painting and coating. It plays a key role in industrial application.

The traditional method for oxime production is hydroxylamine method, which is time-consuming and complicated. It needs to use strong acid having rigorous corrosion resistance requirement for equipment, and likely resulting in many environmental problems. This method is being phased out gradually. The successful development of titanium silicalite molecular sieve (TS-1) initiated an environmental-friendly chemical process based on the zeolite catalyst. The one-step synthesis of oxime product can be realized with ketone ammoximation reaction catalyzed by the TS-1 in the presence of hydrogen peroxide. The method has attracted extensive attention with mild conditions and high reaction efficiency. However, a large volume of solvent like tert-butyl alcohol is added in the ammoximation reaction, and such solvent needs to be recycled in the subsequent process. Consequently, the industrial energy consumption increases, and the use of solvent aggravates the environmental pollution. Therefore, the development of solvent-free ammoximation process has significance on application. The ammoximation reaction is a heterogeneous catalytic process in which mass transfer is greatly affected by solvent. As a result, the key point of solvent-free ammoximation reaction is to realize the effective mass transfer for solution-to-solution and solution-to-catalyst.

Some domestic studies on the solvent-free oxime production method have been carried out: invention patent CN 103288678A and invention patent CN 103288679A use water as the solvent to carry out cyclohexanone ammoximation reaction, but the conversion rate of cyclohexanone is as low as about 40.0%; invention patent CN 103288677A adopts TS-1/CNF composite catalyst and water (solvent) to carry out cyclohexanone ammoximation reaction, which requires expensive composite catalyst and a large amount of water increasing the energy consumption of subsequent oxime-water separation; and invention patent CN 101318912A carries out butanone ammoximation reaction without organic solvent, but the diacetylmonoxime yield is only 70.3%.

SUMMARY OF THE INVENTION

The purpose of the invention is to provide a solvent-free green ammoximation process improving the current processes based on membrane distribution. Consequently, the amount of reactant materials, energy consumption and environmental impact can be greatly reduced in the modified green production process.

The adopted technical scheme on solvent-free ammoximation process in the invention is as follows:

adding TS-1 catalyst and ketone into a reactor in advance, setting stirring speed and reaction temperature; and after reaching the set temperature, feeding hydrogen peroxide using a membrane distributor, feeding ammonia in a continuous or semi-continuous manner.

Preferably, the ketone compound can be cyclohexanone, butanone or acetone. The ammonia source can be ammonium hydroxide or ammonia gas. And the mass concentration of the hydrogen peroxide is 25% to 99%.

The ratio of the mass of TS-1 catalyst over the molar of ketone is 9.0 g/mol to 20.0 g/mol; and the molar ratio of the ketone to the ammonia to the hydrogen peroxide is 1.0: (1.3~2.2):(1.1~1.6).

Preferably, the stirring speed is 600 rpm to 1,000 rpm; and the reaction temperature is 60° C. to 85° C.

Preferably, the ceramic membrane is zirconia membrane, titania membrane, alumina membrane or silicon carbide membrane; and pore size of membrane is 50 nm to 2,000 nm. The membrane flux is preferably 0.12 $m^3 \cdot m^{-2} \cdot h^{-1}$ to 0.20 $m^3 \cdot m^{-2} \cdot h^{-1}$.

Beneficial Effects

In the invention, oxime is produced from the reaction between ketone and hydrogen peroxide and ammonia in the presence of TS-1. The reaction conditions are mild, the efficiency is high, the process is simple; meanwhile, the environmental-friendly production process also reduces material and energy consumption. The conversion rate of ketone and the selectivity of oxime can respectively reach 98.0% or above during the ketone ammoximation reaction without solvent, and water is almost the only by-product.

DETAILED DESCRIPTION OF THE PREFERRED EMBODIMENT

Figure 1:
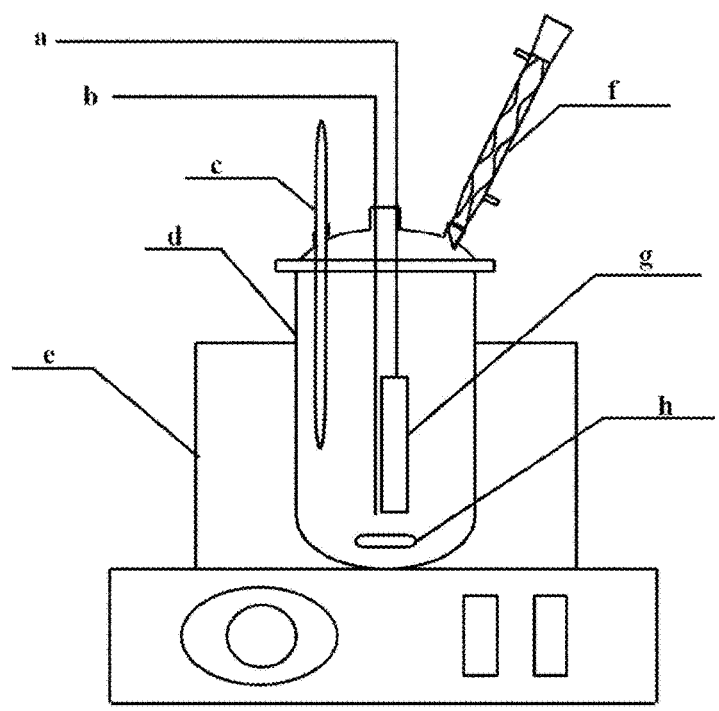
FIG. 1 is a schematic diagram of the reaction device of the invention, wherein, a—hydrogen peroxide solution, b—ammonia, c—thermometer, d—reactor, e—magnetic heating stirrer, f—condensing tube, g—membrane distributor and h—rotor.
Figure 2:
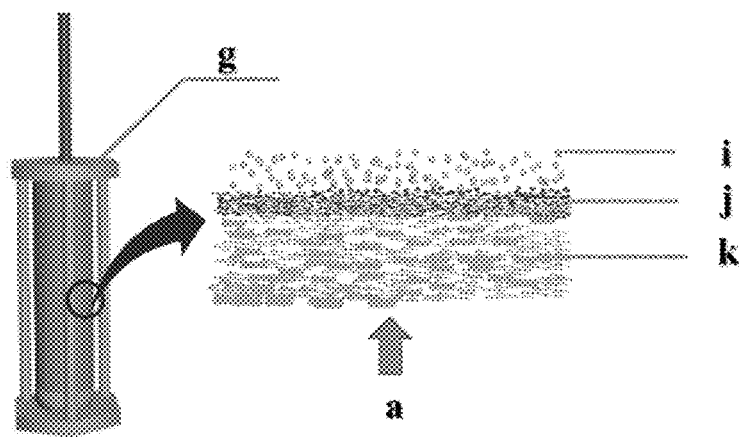
FIG. 2 is a schematic diagram of the membrane distributor of the invention: wherein, g—membrane distributor, a—hydrogen peroxide solution, i—hydrogen peroxide droplet, j—membrane layer and k—support layer.

The schematic diagram of the reaction device of the following embodiments is shown in FIG. 1, wherein, a—hydrogen peroxide solution, b—ammonia, c—thermometer, d—reactor, e—magnetic heating stirrer, f—condensing tube, g—membrane distributor and h—rotor; and the schematic diagram of the membrane distributor is shown in FIG. 2, wherein, g—membrane distributor, a—hydrogen peroxide solution, i—hydrogen peroxide micro-droplet, j—membrane layer and k—support layer. The description of the membrane distributor is referred to "A Novel Dual-Membrane Reactor for Continuous Heterogeneous Oxidation Catalysis" by Hong Jiang, Lie Meng, Rizhi Chen, et al. *Industrial & Engineering Chemistry Research*, 2011, (50), 10458~10464.

Example 1

(1) A catalyst and cyclohexanone were added into the reactor in advance at a ratio of 9.0 g/mol, and the stirring speed was set to be 600 rpm and the reaction temperature was 80° C.

(2) After reaching the set reaction temperature, ammonia and hydrogen peroxide were added into the reaction solution with molar ratio of the cyclohexanone to the ammonia to the hydrogen peroxide of 1.0:1.3:1.3, and the reaction was carried out under atmospheric pressure.
(3) The hydrogen peroxide was fed in a way of using an alumina membrane distributor with mean pore size of 200 nm at limited membrane flux 0.12 $m^3 \cdot m^{-2} \cdot h^{-1}$, and the ammonia was fed in a continuous manner.
(4) After the reaction for 1.5 h, the catalyst was separated for detection analysis of the oxime product. The conversion rate of the cyclohexanone and the selectivity of the cyclohexanone-oxime were calculated to be 98.0% and 100.0% respectively. When the hydrogen peroxide was fed in a way of direct dropwise addition rather than membrane distributing, the conversion rate of the cyclohexanone and the selectivity of the cyclohexanone-oxime were 85.4% and 61.3% respectively.

Example 2

(1) A catalyst and cyclohexanone were added into the reactor in advance at a ratio of 9.0 g/mol, and the stirring speed was set to be 600 rpm and the reaction temperature was 80° C.
(2) After reaching the set reaction temperature, ammonia and hydrogen peroxide were added into the reaction solution at a molar ratio of the cyclohexanone to the ammonia to the hydrogen peroxide of 1.0:1.3:1.1, and the reaction was carried out under atmospheric pressure.
(3) The hydrogen peroxide was fed in a way of using a titania ceramic membrane distributor with mean pore size of 50 nm at limited membrane flux 0.12 $m^3 \cdot m^{-2} \cdot h^{-1}$, and the ammonia was fed in a continuous manner.
(4) After the reaction for 1.5 h, the catalyst was separated for detection analysis of the oxime product. The conversion rate of the cyclohexanone and the selectivity of the cyclohexanone-oxime were calculated to be 83.2% and 100.0% respectively. When the hydrogen peroxide was fed in a way of direct dropwise addition rather than membrane distributing, the conversion rate of the cyclohexanone and the selectivity of the cyclohexanone-oxime were 64.5% and 42.1% respectively.

Example 3

(1) A catalyst and cyclohexanone were added into the reactor in advance at a ratio of 12.0 g/mol, and the stirring speed was set to be 600 rpm and the reaction temperature was 85° C.
(2) After reaching the set reaction temperature, ammonia and hydrogen peroxide were added into the reaction solution at a molar ratio of the cyclohexanone to the ammonia to the hydrogen peroxide of 1.0:1.4:1.4, and the reaction was carried out under atmospheric pressure.
(3) The hydrogen peroxide was fed in a way of using an alumina ceramic membrane distributor with mean pore size of 2,000 nm at limited membrane flux 0.20 $m^3 \cdot m^{-2} \cdot h^{-1}$, and the ammonia was fed in a continuous manner.
(4) After the reaction for 1.5 h, the catalyst was separated for detection analysis of the oxime product. The conversion rate of the cyclohexanone and the selectivity of the cyclohexanone-oxime were calculated to be 81.9% and 99.2% respectively. When the hydrogen peroxide was fed in a way of direct dropwise addition rather than membrane distributing, the conversion rate of the cyclohexanone and the selectivity of the cyclohexanone-oxime were 73.6% and 65.7% respectively.

Example 4

(1) A catalyst and butanone were added into the reactor in advance at a ratio of 15.0 g/mol, and the stirring speed was set to be 1,000 rpm and the reaction temperature was 65° C.
(2) After reaching the set reaction temperature, ammonia and hydrogen peroxide were added into the reaction solution at a molar ratio of the butanone to the ammonia to the hydrogen peroxide of 1.0:1.8:1.25, and the reaction was carried out under atmospheric pressure.
(3) The hydrogen peroxide was fed in a way of using an alumina ceramic membrane distributor with mean pore size of 200 nm at limited membrane flux 0.12 $m^3 \cdot m^{-2} \cdot h^{-1}$, and the ammonia was fed in a semi-continuous manner.
(4) After the reaction for 3.0 h, the catalyst was separated for detection analysis of the oxime product. The conversion rate of the butanone and the selectivity of the diacetylmonoxime were calculated to be 100.0% and 99.0% respectively. When the hydrogen peroxide was fed in a way of direct dropwise addition rather than membrane distributing, the conversion rate of the butanone and the selectivity of the diacetylmonoxime were 86.5% and 40.6% respectively.

Example 5

(1) A catalyst and butanone were added into the reactor in advance at a ratio of 20.0 g/mol, and the stirring speed was set to be 1,000 rpm and the reaction temperature was 60° C.
(2) After reaching the set reaction temperature, ammonia and hydrogen peroxide were added into a reaction solution at a molar ratio of the butanone to the ammonia to the hydrogen peroxide of 1.0:2.0:1.6, and the reaction was carried out under atmospheric pressure.
(3) The hydrogen peroxide was fed in a way of using a zirconia ceramic membrane distributor with mean pore size of 500 nm at limited membrane flux 0.20 $m^3 \cdot m^{-2} \cdot h^{-1}$, and the ammonia was fed in a semi-continuous manner.
(4) After the reaction for 3.0 h, the catalyst was separated for detection analysis of the oxime product. The conversion rate of the butanone and the selectivity of the diacetylmonoxime were calculated to be 100.0% and 92.3% respectively. When the hydrogen peroxide was fed in a way of direct dropwise addition rather than membrane distributing, the conversion rate of the cyclohexanone and the selectivity of the cyclohexanone-oxime were 82.3% and 41.7% respectively.

Example 6

(1) A catalyst and acetone were added into the reactor in advance at a ratio of 18.0 g/mol, and the stirring speed was set to be 700 rpm and the reaction temperature was 65° C.
(2) After reaching the set reaction temperature, ammonia and hydrogen peroxide were added into a reaction solution at a molar ratio of the acetone to the ammonia to the hydrogen peroxide of 1.0:2.2:1.2, and the reaction was carried out under atmospheric pressure.
(3) The hydrogen peroxide was fed in a way of using an alumina ceramic membrane distributor with mean pore size of 200 nm at limited membrane flux 0.12 m³·m⁻²·h⁻¹, and the ammonia was fed in a continuous manner.

(4) After the reaction for 2.5 h, the catalyst was separated for detection analysis of the oxime product. The conversion rate of the acetone and the selectivity of the acetoxime were calculated to be 100.0% and 99.4% respectively. When the hydrogen peroxide was fed in a way of direct dropwise addition rather than membrane distributing, the conversion rate of the acetone and the selectivity of the acetoxime were 22.8% and 78.8% respectively.

Example 7

(1) A catalyst and acetone were added into the reactor in advance at a ratio of 18.0 g/mol, and the stirring speed was set to be 700 rpm and the reaction temperature was 70° C.

(2) After reaching the set reaction temperature, ammonia and hydrogen peroxide were added into a reaction solution at a molar ratio of the acetone to the ammonia to the hydrogen peroxide of 1.0:2.0:1.4, and the reaction was carried out under atmospheric pressure.

(3) The hydrogen peroxide was fed in a way of using a silicon carbide membrane distributor with mean pore size of 50 nm at limited membrane flux 0.20 m³·m⁻²·h⁻¹, and the ammonia was fed in a continuous manner.

(4) After the reaction for 2.5 h, the catalyst was separated for detection analysis of the oxime product. The conversion rate of the acetone and the selectivity of the acetoxime were calculated to be 99.2% and 94.6% respectively. When the hydrogen peroxide was fed in a way of direct dropwise addition rather than membrane distributing, the conversion rate of the cyclohexanone and the selectivity of the cyclohexanone-oxime were 25.4% and 70.7% respectively.

What is claimed is:

1. A solvent-free green ammoximation process based on a membrane distribution includes the following steps:
    adding a TS-1 catalyst and a ketone into a reactor in advance, setting a stirring speed and a reaction temperature; and after reaching the set temperature,
    adding hydrogen peroxide in a way of using membrane as a distributor, and
    adding ammonia in a continuous or semi-continuous manner.

2. The solvent-free green ammoximation process according to claim 1, characterized in that the ketone compound is cyclohexanone, butanone or acetone.

3. The solvent-free green ammoximation process according to claim 1, characterized in that the ammonia is ammonium hydroxide or ammonia gas; and the mass concentration of the hydrogen peroxide is 25% to 99%.

4. The solvent-free green ammoximation process according to claim 1, characterized in that the ratio of the mass of TS-1 catalyst over the molar of ketone is 9.0 g/mol to 20.0 g/mol; and the molar ratio of ketone to ammonia to hydrogen peroxide is 1.0:(1.3~2.2):(1.1~1.6).

5. The solvent-free green ammoximation process according to claim 1, characterized in that the stirring speed is 600 rpm to 1,000 rpm.

6. The solvent-free green ammoximation process according to claim 1, characterized in that the reaction temperature is 60° C. to 85° C.

7. The solvent-free green ammoximation process according to claim 1, characterized in that a ceramic membrane is zirconia membrane, titania membrane, alumina membrane or silicon carbide membrane; and mean pore size of the membrane is 50 nm to 2,000 nm.

8. The solvent-free green ammoximation process according to claim 1, characterized in that the membrane flux if 0.12 m³·m⁻²·h⁻¹ to 0.20 m³·m⁻²·h⁻¹.

* * * * *